US006924098B2

(12) United States Patent
Hu et al.

(10) Patent No.: US 6,924,098 B2
(45) Date of Patent: Aug. 2, 2005

(54) NUCLEIC ACID LADDERS

(75) Inventors: A-Li W. Hu, Kensington, MD (US); James L. Hartley, Frederick, MD (US); Heather J. Jordan, Gaithersburg, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/472,067

(22) Filed: Dec. 23, 1999

(65) Prior Publication Data

US 2003/0099939 A1 May 29, 2003

Related U.S. Application Data

(63) Continuation of application No. 09/048,242, filed on Mar. 26, 1998, now abandoned.
(60) Provisional application No. 60/040,914, filed on Mar. 27, 1997.

(51) Int. Cl.[7] .......................... C12P 19/34; C12N 15/64; C12Q 1/68; C07H 21/02; C07H 21/04
(52) U.S. Cl. ......................... 435/6; 435/91.1; 435/91.4; 435/91.5; 435/320.1; 435/252.3; 536/23.1; 536/24.2
(58) Field of Search .......................... 435/6, 91.1, 91.5, 435/91.4, 320.1, 471; 536/22.1, 23.1, 24.2, 25.3, 25.4

(56) References Cited

U.S. PATENT DOCUMENTS

| | | | |
|---|---|---|---|
| 4,403,036 A | 9/1983 | Hartley et al. | 435/317 |
| 4,415,732 A | 11/1983 | Caruthers et al. | 536/27 |
| 4,458,066 A | 7/1984 | Caruthers et al. | 536/27 |
| 4,500,707 A | 2/1985 | Caruthers et al. | 536/27 |
| 4,668,777 A | 5/1987 | Caruthers et al. | 536/27 |
| 4,900,659 A | 2/1990 | Lo et al. | 435/6 |
| 4,900,659 A | 2/1990 | Hewitt | 435/259 |
| 4,935,357 A | 6/1990 | Szybalski | 435/91 |
| 5,030,566 A | 7/1991 | Son et al. | 435/91 |
| 5,108,179 A | 4/1992 | Myers | 356/344 |
| 5,302,510 A | 4/1994 | Klevan | 435/6 |
| 5,316,908 A | 5/1994 | Carlson et al. | 435/6 |
| 5,714,326 A | 2/1998 | Dawson | 435/6 |
| 5,792,664 A | 8/1998 | Chait et al. | 436/89 |
| 5,824,787 A | * 10/1998 | Singer | 536/22.1 |
| 5,840,575 A | 11/1998 | Hyman | 435/320.1 |

FOREIGN PATENT DOCUMENTS

| | | |
|---|---|---|
| EP | 0 466 404 A1 | 1/1992 |
| WO | WO 91/18095 | 11/1991 |
| WO | WO 93/14224 | 7/1993 |
| WO | WO 94/02647 | 2/1994 |
| WO | WO 95/11971 | 5/1995 |

OTHER PUBLICATIONS

Okazaki, T. et al. Neurobiology of Aging, vol. 16, No. 6, pp. 883–894 (1995).*
Oncor Catalogue: Life for the Living. 1996–1997.*
Bayou Biolabs (Harahan, LA) Products for Molecular Biology 1998 Catalog, "DNA Ladders," pp. 2–7.
Bernards, A., et al., "Pulsed field gradient electrophoresis of DNA digested in agarose allows the sizing of the large duplication unit of a surface antigen gene in trypanosomes," *Chemical Abstracts* 105:187, Abstract No. 92470r (1986).
BRL/Life Technologies Package Insert, "DNA Analysis Marker System" (1990).
Carman, W.F., and C. Williamson, "Detection of Enzymatically Amplified Human Immunodeficiency Virus DNA by Oligonucleotide Solution Hybridization and by Incorporation of Rediolabeled Deoxynucleotides," *J. Clin. Microbiol.* 27:2570–2573 (1989).
GenBank Accession No. J02459, "Bacteriophage Lambda whole Genome," Apr. 23, 1996.
Gensura Laboratories, Inc. Product List Winter 1997–98 for "Superladder dsDNA Markers," including "Superladder–low," "Superladder–mid 1,2," and "Superladder–high." (3 pages).
Gralla, J.D., "Rapid 'footprinting' on supercoiled DNA," *Proc. Natl. Acad. Sci. USA* 82:3078–3081 (1985).
Huang, J. et al., "Restriction endonuclease analysis of granulosis virus DNA of *Agrotis exclamationis* Linnaeus," *Chemical Abstracts* 107:175, Abstract No. 34093a (1987).
Invitrogen (Carlsbad, CA) 1997 Product Catalog, "DNA Molecular Weight Markers," p. 113.
Jones, C.P. et al., "Separation of yeast chromosomes in the megabase range suitable as size markers for pulsed–field gel electrophoresis," *Chemical Abstracts* 112:172, Abstract No. 230760h (1990).
Life Technologies 1995 Gibco BRL Catalog, pp. 14–2, 14–6, 15–14, R–90 (1995).
Life Technologies 1997 Gibco BRL Catalog, p. 16–2 (1997).
Life Technologies, Inc. (Gaithersburg, MD) GIBCO BRL 1997/1998 Products and Reference Guide, "500 bp Ladder" and "1 Kb DNA Ladder," p. 16–5.

(Continued)

*Primary Examiner*—John L. LeGuyader
*Assistant Examiner*—Jane Zara
(74) *Attorney, Agent, or Firm*—Sterne, Kessler, Goldstein & Fox, P.L.L.C.

(57) ABSTRACT

The present invention provides nucleic acid molecules which may be used as standards for estimating the size (in base pairs) and mass of linear, double-stranded or single-stranded nucleic acid molecules separated by size. The nucleic acid molecules of the invention may be DNA molecules, RNA molecules or DNA/RNA hybrid molecules, and may be double-stranded or single-stranded. The invention also provides methods for producing nucleic acid sizing ladders from these nucleic acid molecules, ladders produced by such methods, and methods for estimating the size and mass of nucleic acid molecules by comparison to these nucleic acid sizing ladders.

43 Claims, 3 Drawing Sheets

OTHER PUBLICATIONS

Mathew, M.K. et al., "High–Resolution Separation and Accurate Size Determination in Pulsed–Field Gel Electrophoresis of DNA. 1. DNA Size Standards and the Effect of Agarose and Temperature," *Biochemistry* 27:9204–9210 (1988).

Minter, S. and P. Sealey, "Appendix 1: Nucleic Acid Molecular Weight Markers," In: *Gel Electrophoresis of Nucleic Acids: A Practical Approach*, Rickwood, D. and B.D. Hames, eds., IRL Press, Washington, D.C., pp. 227–232 (1982).

Novagen 1997 Catalog, Published by Novagen, Milwaukee, WI, pp. 4–5, 115–117.

Pharmacia LKB Biotechnology (Piscataway, NJ), 1990 Molecular and Cell Biology Price List, "Molecular Weight Markers," p. 23.

Pharmacia Biotech (Piscataway, NJ) 1997 Biodirectory Product Catalog, "KiloBase DNA Marker" p. 58.

Promega (Madison, WI), 1990 Products Catalog, "Lambda ECORI Markers," p. 238.

Promega (Madison, WI), 1997 Biological Research Products Catalog, "1kb DNA Ladder," p. 17.

Sigma (St. Louis, MO), 1997 Biochemicals and Reagents for Life Science Research Catalog, "DNA/RNA Analysis Products," p. 1530.

Stratagene (La Jolla, CA), 1988 Catalog, pp. 55–57, 100, 123.

Stratagene (La Jolla, CA) 1997/1998 Catalog, "Kb DNA Ladder," p. 130.

Dialog File 351, English Language abstract of Japanese Patent No. 63–113359 (Doc. AL1), Derwent WPI Accession No. 88–177809/26 (1988).

* cited by examiner

NUCLEIC ACID LADDERS

CROSS REFERENCE TO RELATED APPLICATION

The present application is a continuation of U.S. application Ser. No. 09/048,242, filed Mar. 26, 1998 now abandoned, which claims priority to U.S. Provisional Application No. 60/040,914, filed Mar. 27, 1997, the contents of which are entirely incorporated herein by reference.

FIELD OF THE INVENTION

The present invention is in the field of molecular biology. In particular, the invention relates to determining the size of nucleic acid molecules by comparing such nucleic acid molecules to a nucleic acid marker ladder (single- or double-stranded) having a known size.

BACKGROUND OF THE INVENTION

Electrophoresis

A common method of analyzing nucleic acid (e.g., DNA or RNA) fragments is by separation in an agarose or polyacrylamide gel matrix. Such matrices provide a medium in which such fragments of different sizes and forms may be analyzed. In the presence of an electrical current, nucleic acid fragments will migrate through such a gel matrix in the direction of the positive electrode. Since small, linear nucleic acid molecules migrate more easily and quickly through the pores of the gel than do larger molecules, the matrix acts as a molecular sieve, separating fragments of different sizes. Larger nucleic acid fragments are typically electrophoresed on low concentration agarose gels, while smaller fragments are separated on higher concentration agarose gels or on polyacrylamide gels, since polyacrylamide has a higher resolution capacity than agarose.

Detection of Nucleic Acid Fragments

Detection of nucleic acid molecules electrophoresed in agarose or polyacrylamide gels can be accomplished by a variety of techniques, including the use of fluorescent dyes such as ethidium bromide and SYBR Green. These dyes bind to the nucleic acid molecules and fluoresce when exposed to UV light. Alternatively, the nucleic acid molecules can be detectably labeled by chemically coupling them with radioactive, fluorescent or chemiluminescent labels.

Sizing Standards

For the purpose of analyzing nucleic acid fragments on agarose or polyacrylamide gels, nucleic acid molecular weight standards are very useful tools, providing the researcher with a point of reference for estimating the quality, size, and/or quantity of the nucleic acid sample. A standard is typically run simultaneously on the gel with the sample (e.g., in parallel with the sample), and following detection, a comparison is made between the sample band(s) and the bands of the standard. Knowing the size (in base pairs) of the standard allows the size of the unknown fragment(s) to be estimated.

Common standards used for estimating the size of nucleic acid fragments on gels include naturally occurring genomic DNA of bacteriophages (e.g., lambda bacteriophage and φX174). To prepare such standards, the phage genomic DNA is cleaved into a population of nucleic acid fragments of known size using a specific restriction endonuclease. These types of standards are commonly called "nucleic acid markers" (e.g., "DNA markers").

Another type of nucleic acid standard is produced by engineering plasmids to contain recognition/cleavage sites for one or more specific restriction endonucleases at particular intervals in the plasmid. See, e.g., WO 95/11971. Upon digestion of the plasmid with the specific endonuclease(s), nucleic acid fragments of specific known sizes are generated. For accuracy in size determination and for ease of use, it is beneficial to have numerous bands that increase in size in regular, even intervals. The bands of the standard should also be able to be detected with equivalent intensity. These types of standards are commonly called "nucleic acid ladders" (e.g., "DNA ladders").

A 10 bp DNA ladder which consists of a set of twenty fragments containing repeats of a 10 bp sequence is commercially available from Life Technologies, Inc. (Gaithersburg, Md.). This ladder is constructed by ligation of synthetic double-stranded oligonucleotides, and is not generated from a plasmid. The multimers in the ladder contain multiple deoxyuracil bases in one strand and can be converted to a single-stranded form by incubation with uracil DNA glycosylase (UDG), which degrades the uracil-containing strand. Bands at 10 bp and 100 bp are highlighted for orientation within the standard.

This 10 bp DNA ladder can be used for sizing double-stranded DNA, or treated with UDG as described above for sizing single-stranded DNA, and may be stained with ethidium bromide or end-labeled with T4 polynucleotide kinase. However, due to the nature of the production procedure (ligation of oligonucleotides), it is not amenable to fluorescent detection, nor is it useful for Amplification Fragment Length Polymorphism (AFLP) analysis (Vos et al., *Nucl. Acids. Res.* 23:4407–4414 (1995)), primarily because the resulting range of fragment sizes is too low and the electrophoretic bands are not sharply resolved.

Other commercially available products include a 20 bp DNA ladder sold by GenSura, a 20 bp DNA ladder sold by Invitrogen (these may be the same product sold by the two companies), and LTI's 25 bp ladder. The LTI 25 bp DNA ladder is derived from a plasmid engineered to contain several repeats of a 25 bp sequence which can be digested by restriction enzymes to generate bands increasing in size by 25 bp. The repeated sequence in the LTI 25 bp DNA ladder, however, can be used only for sizing double-stranded DNA.

BRIEF SUMMARY OF THE INVENTION

The present invention relates to a nucleic acid molecule comprising two or more copies of a repeat-containing sequence having the formula $(X_1X_2)_n$ $(Y_1Y_2)_n$ wherein:

$X_1$ and $X_2$ are single nucleotides or derivatives thereof which may or may not be identical;

$Y_1$ and $Y_2$ are single nucleotides or derivatives thereof complementary to $X_1$ and $X_2$, respectively; and n is an integer from 1 to $1 \times 10^{10}$, and wherein two or more of the repeat-containing sequence copies are separated by a restriction site and the nucleotide compositions of $(X_1X_2)_n$ and $(Y_1Y_2)_n$ are substantially identical. The invention also relates to a nucleic acid molecule comprising two or more copies of a repeat-containing sequence having the formula $(X_1X_2)_nA_m$ $B_m(Y_1Y_2)_n$ wherein:

$X_1$ and $X_2$ are single nucleotides or derivatives thereof which may or may not be identical;

$Y_1$ and $Y_2$ are single nucleotides or derivatives thereof complementary to $X_1$ and $X_2$, respectively;

n is an integer from 1 to $1\times10^{10}$;

A is a nucleotide or a derivative thereof;

B is a nucleotide or a derivative thereof; and m is an integer from 1 to 100, wherein two or more of the repeat-containing sequence copies are separated by a restriction site and wherein the nucleotide compositions of $(X_1X_2)_nA_m$ and $B_m(Y_1Y_2)_n$ are substantially identical. The invention is particularly directed to such nucleic acid molecules which are DNA molecules, RNA molecules, or DNA/RNA hybrid molecules, and to such molecules which may be double-stranded.

In another aspect, the invention is directed to such molecules wherein tvvo or more of the repeat-containing sequence copies are separated by cleavage at the restriction site. In preferred such aspects, 2 to 500, 2 to 100 or 2 to 50 of said repeat-containing sequence copies are separated by cleavage at said restriction site. The invention is also directed to such separated repeat-containing sequence copies which are detectably labeled or which are subjected to conditions favoring the conversion of the sequences into a single-stranded form which may themselves be detectably labeled. Preferred detectable labels for this aspect of the invention include radiolabels, fluorescent labels and chemiluminescent labels.

The invention is also directed to the above-described nucleic acid molecules, wherein each of the repeat-containing sequence copies are the same length. In particular, the invention is directed to such nucleic acid molecules wherein each of the repeat-containing sequence copies has a length of from about 5 nucleotides to about 1000 nucleotides and more preferably a length of from about 5 nucleotides to about 100 nucleotides.

The invention is also directed to the above-described nucleic acid molecules wherein $(X_1X_2)$ and $(Y_1Y_2)$ are identical, and to those wherein the repeat-containing sequence is a palindromic sequence.

The invention is also directed to the above-described nucleic acid molecules wherein the nucleotides or derivatives thereof are selected from the group consisting of dUTP, dATP, dTTP, dCTP, dGTP, dITP, 7-deaza-dGTP, αdATP, αdTTP, αdGTP, αdCTP, ddATP, ddTTP, ddCTP and ddGTP. In additional preferred nucleic acid molecules of the invention, n is an integer from 1 to $1\times10^6$. In other preferred nucleic acid molecules of the invention, n is an integer from 1 to $1\times10^3$ and m is an integer from 1 to 10.

The invention is also directed to vectors comprising the above-described nucleic acid molecules, particularly the plasmid vector pAH102.4. The invention is also directed to a host cell comprising the above-described nucleic acid molecules or vectors.

The invention is also directed to nucleic acid ladders comprising the above-described nucleic acid molecules. The invention also provides methods for making additional nucleic acid ladders, a preferred such method comprising (a) mixing the above-described nucleic acid molecule with a restriction enzyme which cleaves at the restriction site; and (b) incubating the mixture under conditions favoring the cleavage of the nucleic acid molecule at one or more of the restriction sites. Preferably, such cleavage is a partial digestion to form a population of multimers (e.g., monomer repeat, dimer repeat, trimer repeat, tetramer repeat, etc.), thereby forming a ladder. In a preferred such aspect, the invention provides such methods further comprising treating the nucleic acid molecule under conditions favoring the conversion of the nucleic acid molecule into a single-stranded form.

The invention also provides methods for determining the size of a nucleic acid molecule, a preferred such method comprising (a) separating the nucleic acid ladder of the invention, and the nucleic acid molecule to be sized, according to size; and (b) determining the size of the nucleic acid molecule by comparison to the nucleic acid ladder.

The invention also relates to kits comprising a carrier means, such as a box, carton or the like, being compartmentalized to receive in close confinement therein one or more container means, such as tubes, vials, ampules, bottles or the like, wherein a first container means comprises the nucleic acid molecule or ladder of the present invention.

DETAILED DESCRIPTION OF THE INVENTION

Figure 1:
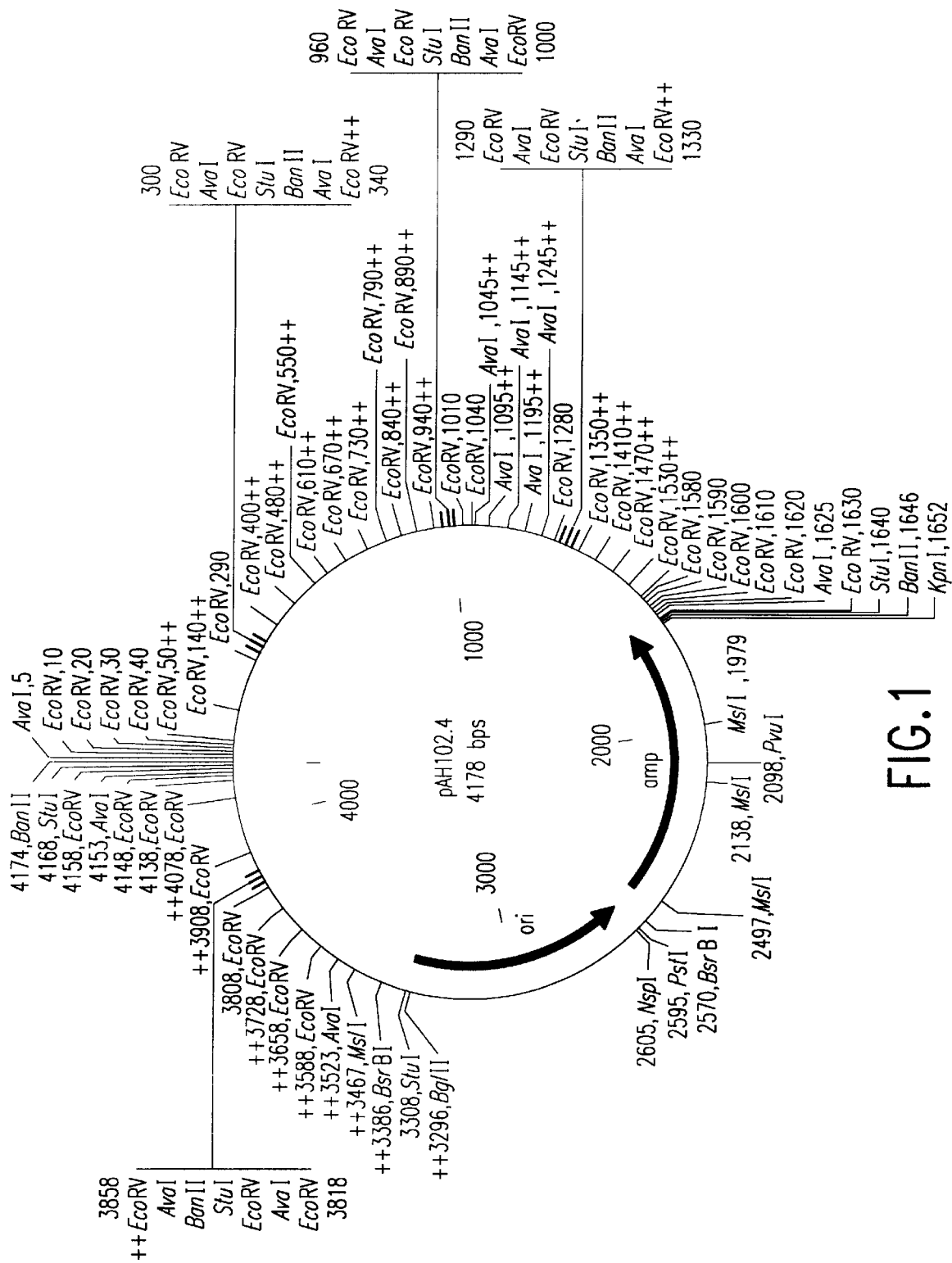
FIG. 1 depicts a plasmid map of pAH102.4 described in Example 1.

The present invention relates to nucleic acid molecules which may be used as standards for estimating the size (in base pairs) and mass of linear, double-stranded or single-stranded nucleic acid molecules separated by size, preferably by electrophoresis on agarose or polyacrylamide gels. The nucleic acid molecules of the invention may be DNA molecules, RNA molecules or DNA/RNA hybrid molecules, and may be double-stranded or single-stranded.

In particularly preferred aspects of the invention, the nucleic acid molecules are produced from vectors designed to contain at least two copies, preferably about 2 to about 500 copies, 20 to 100 copies or 2 to 50 copies, and most preferably about 200 to about 300 copies, of a repeat-containing sequence. The repeat-containing sequences contained in the nucleic acid molecules of the invention are preferably about 5 to about 1000 nucleotides (for single-stranded nucleic acid molecules) or base pairs (for double-stranded nucleic acid molecules) in length, and most preferably about 5–100 nucleotides or base pairs in length. In a preferred aspect of the invention, each of the repeat-containing sequences is of the same size (i.e., length). In another preferred aspect of the invention, the repeat-containing sequences have the same base compositions in the top and bottom strands. The repeat-containing sequences having the same base composition may be palindromic sequences, where the sequence of the top and bottom strands are mirror images. According to the invention, the top and bottom strands of the repeat-containing sequence need only be substantially identical in base composition. By "substantially identical in base composition" is meant that the top and bottom strands of the repeat-containing sequence are about 80%, preferably at least about 90%, more preferably at least about 95%, still more preferably at least about 98% or about 99%, and most preferably at least about 100%, identical in base composition. Although substantially identical base compositions include palindromic sequences, the order of the sequence in the top and bottom strand need not be the same according to the invention.

Example repeat-containing sequences of the invention include but are not limited to:

```
ATCTCAGGAT                              (SEQ ID NO:1)
TAGAGTCCTA

ATCAGTCGAT                              (SEQ ID NO:2)
TAGTCAGCTA

ATCGCATGAT                              (SEQ ID NO:3)
TAGCGTACTA

ATCATGCGAT                              (SEQ ID NO:4)
TAGTACGCTA
```

According to this aspect of the invention, a particularly preferred nucleic acid molecule contains about 231 repeats, each of which is about 5–100 nucleotides or base pairs in length. The size of the repeats is preferably selected to be a multiple of an integer, wherein the integer is two or more. In one preferred embodiment, the integer is 10, 50 or 100m. More preferably, the repeat sequence is a 10 bp sequence.

In order to prepare the repeat-containing nucleic acid molecules of the invention, one may first prepare an oligonucleotide that contains multiple copies of a repeat. The oligonucleotide may be prepared by methods of solid phase synthesis or other methods suitable for synthesis of oligonucleotide molecules that will be apparent to one of ordinary skill in the art.

According to one aspect of the invention, a preferred such oligonucleotide may be represented by the Formula (I):

$(X_1X_2)_n$ $(Y_1Y_2)_n$ (I)

wherein:

$X_1$ and $X_2$ are single nucleotides or derivatives thereof which may or may not be identical;

$Y_1$ and $Y_2$ are single nucleotides or derivatives thereof complementary to $X_1$ and $X_2$, respectively; and n is an integer from 1 to $1\times10^{10}$.

In particularly preferred nucleic acid molecules of this aspect of the invention, $X_1$ and $X_2$ are not identical. In other particularly preferred nucleic acid molecules of this aspect of the invention, two or more of the repeat-containing sequence copies represented by $X_1X_2$ and $Y_1Y_2$ are separated by a restriction site, and the nucleotide compositions of $(X_1X_2)_n$ and $(Y_1Y_2)_n$ are substantially identical. Preferably, the nucleotide compositions of $(X_1X_2)$ and $(Y_1Y_2)$ are the same. In other particularly preferred nucleic acid molecules of this aspect of the invention, n is an integer from 1 to $1\times10^6$.

According to another aspect of the invention, an alternative preferred oligonucleotide may be represented by the Formula (II):

$B_m(Y_1Y_2)_n$ (II)

wherein:

$X_1$ and $X_2$ are single nucleotides or derivatives thereof which may or may not be identical;

$Y_1$ and $Y_2$ are single nucleotides or derivatives thereof complementary to $X_1$ and $X_2$, respectively;

n is an integer from 1 to $1\times10^{10}$;

A is a nucleotide or a derivative thereof;

B is a nucleotide or a derivative thereof; and m is an integer from 1 to 100.

In particularly preferred nucleic acid molecules of this aspect of the invention, $X_1$ and $X_2$ are not identical. In other particularly preferred nucleic acid molecules of this aspect of the invention, two or more of the repeat-containing sequences represented by $X_1X_2$ and $Y_1Y_2$ are separated by a restriction site, and the nucleotide compositions of $(X_1X_2)_nA_m$ and $B_m(Y_1Y_2)_n$ are substantially identical. Preferably, the nucleotide composition of $(X_1X_2)_nA_m$ and $B_m(Y_1Y_2)_n$ are the same. In other particularly preferred nucleic acid molecules of this aspect of the invention, n is an integer from 1 to $1\times10^3$ and m is an integer from 1 to 10.

According to the invention, nucleotides or derivatives thereof suitable for preparing the oligonucleotides and nucleic acid molecules of the invention include, but are not limited to, dUTP, dATP, dTTP, dCTP, dGTP, dITP, ATP, TTP, UTP, GTP, CTP, 7-deaza-dGTP, αdATP, αdTTP, αdGTP, αdCTP, ddATP, ddTTP, ddCTP and ddGTP. Other nucleotides (deoxy and dideoxy) and derivatives thereof suitable for use in forming the nucleic acid molecules of the invention will be familiar to one of ordinary skill in the art.

The repeat-containing sequences of the invention may be ligated to produce multiple repeats. Since such repeats are separated by restriction sites according to the invention, one or more of these repeats may subsequently be separated by cleavage with a restriction enzyme such as a blunt-end or sticky-end restriction endonuclease. A restriction endonuclease is an enzyme that has the capacity to recognize a specific base sequence (usually 4, 5, or 6 base pairs in length) in a DNA molecule, and to cleave the DNA molecule where this sequence appears. In the practice of the present invention, restriction enzymes and restriction sites should be chosen which give identical blunt-end or sticky-end fragments. Examples of blunt-end restriction enzymes suitable for use in the invention, and their cleavage sites, include without limitation:

```
AluI            5'-AG↓CT-3'
                3'-TC↑GA-5'

DraI            5'-TTT↓AAA-3'
                3'-AAA↑TTT-5'

Eco47 III       5'-AGC↓GCT-3'
                3'-TCG↑CGA-5'

EcoRV           5'-GAT↓ATC-3'
                3'-CTA↑TAG-5'

FspI            5'-TGC↓GCA-3'
                3'-ACG↑CGT-5'

HpaI            5'-GTT↓AAC-3'
                3'-CAA↑TTG-5'

MscI            5'-TGG↓CCA-3'
                3'-ACC↑GGT-5'

NruI            5'-TCG↓CGA-3'
                3'-AGC↑GCT-5'

PvuII           5'-CAG↓CTG-3'
                3'-GTC↑GAC-5'
```

| | |
|---|---|
| RsaI | 5'-GT↓AC-3'<br>3'-CA↑TG-5' |
| ScaI | 5'-AGT↓ACT-3'<br>3'-TCA↑TGA-5' |
| SmaI | 5'-CCC↓GGG-3'<br>3'-GGG↑CCC-5' |
| SspI | 5'-AAT↓ATT-3'<br>3'-TTA↑TAA-5' |
| StuI | 5'-AGG↓CCT-3'<br>3'-TCC↑GGA-5' |
| ThaI | 5'-CG↓CG-3'<br>3'-GC↑GC-5' |
| DraI | 5'-TTT↓AAA-3'<br>3'-AAA↑TTT-5' |

Examples of sticky-end restriction enzymes suitable for use in the invention, and their cleavage sites, include without limitation:

| | |
|---|---|
| AvaI | 5'-C↓PyCGPuG-3'<br>3'-GPuGCPy↑C-5' |
| BamHI | 5'-G↓GATCC-3'<br>3'-CCTAGT↑G-5' |
| BanII | 5'-GPuGCPy↓C-3'<br>3'-C↑PYCGPuG-5' |
| BglII | 5'-A↓GATCT-3'<br>3'-TCTAG↑A-5' |
| ClaI | 5'-AT↓CGAT-3'<br>3'-TAGC↑TA-5' |
| EcoRI | 5'-G↓AATTC-3'<br>3'-CTTAA↑G-5' |
| HindIII | 5'-A↓AGCTT-3'<br>3'-TTCGA↑A-5' |
| HpaII | 5'-C↓CGG-3'<br>3'-GGC↑C-5' |
| KpnI | 5'-GGTAC↓C-3'<br>3'-C↑CATGG-5' |
| MseI | 5'-T↓TAA-3'<br>3'-AAT↑T-5' |
| NcoI | 5'-C↓CATGG-3'<br>3'-GGTAC↑C-5' |
| NdeI | 5'-CA↓TATG-3'<br>3'-GTAT↑AC-5' |
| NotI | 5'-GC↓GGCCGC-3'<br>3'-CGCCGG↑CG-5' |
| PstI | 5'-CTGCA↓G-3'<br>3'-G↑ACGTC-5' |
| PvuI | 5'-CGAT↓CG-3'<br>3'-GC↑TAGC-5' |
| SacI/SstI | 5'-GAGCT↓C-3'<br>3'-C↑TCGAG-5' |
| SalI | 5'-G↓TCGAC-3'<br>3'-CAGCT↑G-5' |
| XbaI | 5'-T↓CTAGA-3'<br>3'-AGATC↑T-5' |
| XhoI | 5'-C↓TCGAG-3'<br>3'-GAGCT↑C-5' |

The above-mentioned restriction enzymes, and others that may be equivalently used in the present invention, are available commercially, for example from Life Technologies, Inc. (Rockville, Md.). See also Roberts, R. J., Nucl. Acids Res. 17(Suppl.):r347–r387 (1989), for other examples of restriction enzymes and their cleavage sites.

As will be understood by those of ordinary skill in the art, the nucleic acid molecules used to form the nucleic acid sizing ladder of the invention are preferably linear or circular DNA molecules which are cleavable by a restriction enzyme. For example, the nucleic acid molecules may be derived from a chromosome, a vector, a cosmid, a plasmid or a viral genome. Preferably, the nucleic acid molecules are vector or viral molecules and derivatives thereof The nucleic acids present in the vector or viral molecule may include exogenous nucleic acids which have been joined to produce the vector or viral molecule. In one preferred embodiment, the nucleic acid is DNA.

Preferably, the nucleic acid molecule contains an origin of replication (for example, ori) such that the nucleic acid molecule may autonomously replicate within a host cell. It is also preferable that the nucleic acid molecule contains a selectable or screenable marker. The origin of replication and the marker may be present on the same fragment. Host cells containing the nucleic acid molecule of the invention may be cultured and selected with a selection agent corresponding to the selectable marker.

According to the invention, the repeat sequences may be ligated into a vector which is then transformed into a host cell, the host cell is cultured, lysed and the vector isolated by well known techniques. The vector may then be cut with the restriction endonuclease that recognizes a restriction endonuclease site, thereby separating the repeats to give multiple copies of the repeat fragment. These multiple copies may be ligated together to form multimers, e.g., dimers, trimers, tetramers, pentamers, hexamers and the like. Alternatively, partial digestion of the vector provides for multimers of varying sizes. Such multimers of variable size (e.g., monomers, dimers, trimers, etc.) are used as sizing ladders according to the invention. Such sizing ladders may be double-stranded or single-stranded. Single-stranded ladders may be formed from double-stranded nucleic acid molecules or ladders of the invention by techniques that are well-known to one of ordinary skill in the art, such as heat or chemical denaturation.

As described in more detail in Example 1 below, preferred nucleic acid ladder may be produced from the plasmid pAH102.4 (FIG. 1) by first digesting the plasmid to completion with StuI to generate two copies of a 100 bp sequence and seven "cassettes" each containing 33 10-bp repeats (see FIG. 1). The cassettes are then partially digested with EcoRV restriction enzyme to generate fragments increasing in size by increments of 10 bp, the largest fragment being 330 bp. The 100 bp fragment acts as an internal orientation marker within the ladder by increasing the brightness of the 100 bp band two to three times compared with the other bands in the ladder. Of course, the steps of complete digestion and partial digestion may be reversed in sequence.

The sizing ladder of the present invention can be used for estimating the size (in bp) of double-stranded nucleic acid (e.g., DNA or RNA) fragments, preferably by electrophoresis on agarose or native polyacrylamide gels. This ladder can also be used to size single-stranded nucleic acid fragments when the strands are separated by heat or chemical denaturation. In particular, the 10 bp ladder containing the repeat sequence of SEQ ID NO:1 is useful as a standard for sizing linear, double-stranded and single-stranded nucleic acid fragments in the 10 bp to 330 bp range. The ladder of the present invention can also be detectably labeled, for example with a radiolabel, fluorescent label or chemiluminescent label as described below, and used as a standard in nucleic acid polymorphism analyses such as AFLP (EP 0 534 858; Vos, P. et al, *Nucl. Acids Res.* 23(21):4407–4414 (1995)), Random Amplified Polymorphic DNA (RAPD; Williams, J. G. K. et al., *Nucl. Acids Res.* 18(22):6531–6535 (1990)), DNA Amplification Fingerprinting (DAF; Caetano-Anollés et al., *Bio/Technology* 9:553–557 (1991)) and microsatellite PCR or Directed Amplification of Minisatellite-region DNA (DAMD; Heath, D. D. et al., *Nucl. Acids Res.* 21(24):5782–5785 (1993)). Alternatively, the ladder of the invention may be used as a reference in unlabeled versions of the above-described techniques.

The nucleic acid marker ladder of the present invention may be single-stranded or double-stranded. The double-stranded ladder is obtained directly from the double-stranded nucleic acid construct of the invention. Single strands may be obtained by heating the double-stranded nucleic acid construct of the invention, or by treating it with a chaotropic agent or with a helicase. Alternatively, single strands will be obtained when separating the ladder on SDS-PAGE.

The migration of nucleic acid fragments on polyacrylamide gels is influenced by nucleotide base composition as well as size; that is, two nucleic acid bands containing the same number of base pairs but different nucleotide base compositions may migrate differently on polyacrylamide gels. According to the present invention, the base composition of the top strand of the repeat of the ladder is substantially the same as the base composition of the bottom strand, so the two nucleic acid strands will migrate identically when separated on denaturing polyacrylamide gels. Preferably, the base composition of the top and bottom strands are the same, for example, as with palindromic nucleic acid sequences. This is a major advantage over the known ladders which give rise to substantially different top and bottom single strands when separated.

The ladder bands can be detectably labeled by staining with ethidium bromide or SYBR Green, or by end-labeling using T4 polynucleotide kinase. Thus, another aspect of the invention relates to the ladder of the present invention which is detectably labeled with a stain or other detectable label. Labels suitable for detectably labeling the ladder of the invention include, but are not limited to, radiolabels (e.g., $^{32}P$, $^{14}C$, $^{3}H$ and the like), fluorescent labels (e.g., fluorescein, rhodamine, phycocyanin and the like) and chemiluminescent labels (e.g., using the PHOTO-GENE™ or ACES™ chemiluminescence systems, available commercially from Life Technologies, Inc., Rockville, Md.).

In another embodiment, the present invention relates to a nucleic acid marker kit comprising a carrier means such as a box or carton having in close confinement therein at least one container means such as vials, tubes, jars, ampules and the like. A first container means may comprise the nucleic acid molecule or ladder of the present invention, in optionally labeled form. The first container means may also comprise a storage buffer such as about 10 mM TRIS-HCl (pH 8.0), about 1 mM EDTA and, optionally, about 50 mM NaCl. The nucleic acid marker ladder may be present at a concentration of about 1 μM, and is preferably stored at about −20° C. until use. A further container means may contain a reagent capable of detectably labeling the ladder of the present invention, such as ethidium bromide, SYBR Green, or T4 polynucleotide kinase.

Having now generally described the invention, the same will be more readily understood through reference to the following Examples which are provided by way of illustration, and are not intended to be limiting of the present invention, unless specified.

EXAMPLES

Example 1

Preparation of the Nucleic Acid Ladder

The plasmid pAH102.4 (FIG. 1) was prepared as follows. A 65 bp oligonucleotide molecule was synthesized having the following sequence (SEQ ID NO:5):

```
5'-AATTCTCGGG ATATCTCAGG ATATCTCAGG ATATCTCAGG
   3'-GAGCCC TATAGAGTCC TATAGAGTCC TATAGAGTCC

ATATCTCAGG ATATCTCGGG CTGCA-3'
TATAGAGTCC TATAGAGCCC G-5'
```

The synthesized oligonucleotide was ligated into the pUC18 plasmid (Life Technologies, Inc., Rockville, Md.) between the EcoRI and PstI cloning sites to give plasmid pUC1810a. This plasmid was then cut with AvaI to generate a 50 bp DNA fragment containing five repeats of the 10 bp sequence (SEQ ID NO:1):

```
5'-ATCTCAGGAT-3'

3'-TAGAGTCCTA-5'
```

A new plasmid, pAH102.1, was generated from pUC19 by retaining the origin of replication and amp genes of pUC19, and modifying its multiple cloning sites to contain restriction sites for KpnI, StuI, EcoRV, AvaI, BanII, HindIII, EcoRI and BglII. A series of repeats of the 50 bp fragment was inserted into the AvaI site of plasmid pAH102.1 by adding an excess amount of the 50 bp fragment in the ligation reaction mixture. A plasmid containing a hexamer of the 50 bp DNA was selected by direct size measurement of the DNA fragments of the resulting clones. This hexamer-containing plasmid was designated pAH102.2, and was cleaved with BanII to generate a 330 bp fragment. A series of repeats of this 330 bp fragment was inserted into the BanII site of pAH102.2 and a plasmid containing a heptamer of the 330 bp fragment and 42 copies of the 50 bp fragment was selected and designated as plasmid pAH102.3.

A DNA fragment containing three StuI restriction sites at 100 bp intervals was generated by amplifying phage λ DNA (Life Technologies, Inc., Rockville, Md.) from position 31,384 to position 31,571 using the following primers:

```
Primer I:
                                       (SEQ ID NO:6)
5'-CAA CAA CAA GAA TTC AGG CCT AGC CAG TGC CTC GTC
CAT TTT T-3'

Primer II:
                                       (SEQ ID NO:7)
5'-CAA CAA CAA AAG CTT CTT ACA TGG CCC AGG TGC AGT
A-3'
```

This PCR-amplified λ DNA fragment was cleaved with EcoRI and HindIII and inserted into plasmid pAH102.3 between the engineered EcoRI and HindIII sites to give the desired plasmid, designated pAH102.4 (see FIG. 1). The recombinant host cell comprising pAH102.4, *E. coli* STBL2 (pAH102.4), was deposited on Mar. 26, 1997, with the Collection, Agricultural Research Culture Collection (NRRL), 1815 North University Street, Peoria, Ill. 61604 USA, as Deposit No. NRRL B-21674.

The 10 bp ladder was produced from pAH102.4 by first digesting the plasmid to completion with StuI, thereby releasing two copies of a 100 bp sequence and seven "cassettes" each containing 33 10 bp repeats. The cassettes were partially digested with EcoRV, carefully monitoring the enzyme concentration and incubation time such that the conditions favored the generation of fragments increasing in size in 10 bp increments, the largest fragment being 330 bp. In this ladder, the 100 bp fragment exhibited a density two to three times higher than that of the other bands in the ladder; this fragment thus acts as an internal orientation marker within the ladder.

Example 2

Comparison of the 10 bp Ladder to Commercially Available Ladders

To further characterize the nucleic acid ladder of the invention, the electrophoretic pattern of the double-stranded ladder was compared to that of several commercially available nucleic acid ladders. LTI's 25 bp ladder (1 μg, lane 1); LTI's 10 bp ladder (2 μg, lane 2); the 10 bp ladder produced according to Example 1 (2 μg, lane 3); GenSura's Superladder-Low™ 20 bp ladder (1 μg, lane 4), and Invitrogen's 20 bp ladder (0.8 μg, lane 5) were applied to a 4% LMP agarose gel containing 0.5 μg/ml ethidium bromide. The ladders where electrophoresed for 3.5 h at 75 V in a GIBCO BRL HORIZON® 11.14 apparatus.

Figure 2:
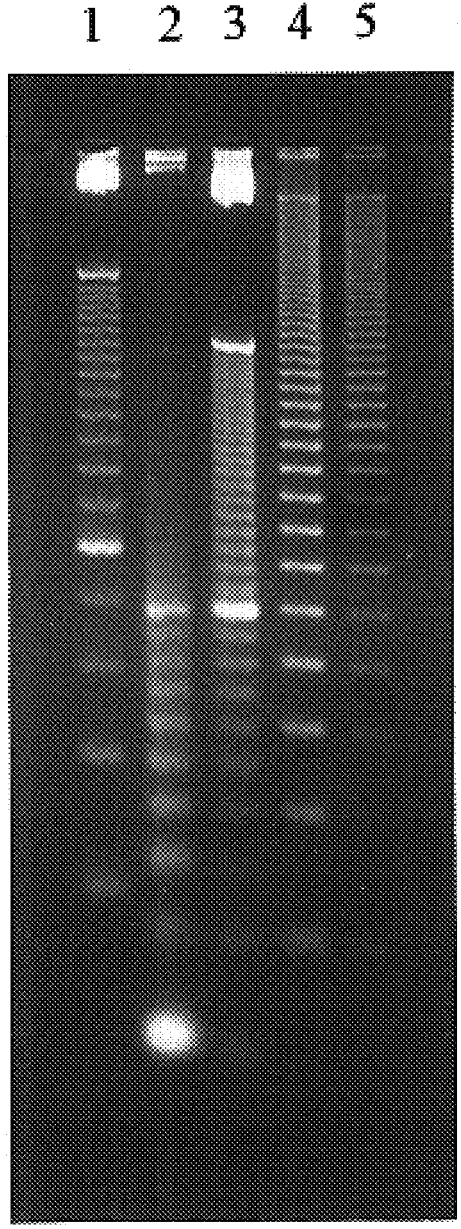
FIG. 2 depicts a gel showing a comparison of the 10 bp ladder of the present invention to various commercially available ladders. Lane 1: 25 bp commercial ladder (Life Technologies, Inc.). Lane 2: 10 bp commercial ladder (Life Technologies, Inc.). Lane 3: 10 bp ladder of the present invention. Lane 4: 20 bp Superladder-Low™ commercial ladder (GenSura). Lane 5: 20 bp commercial ladder (Invitrogen).

As shown in FIG. 2, the 10 bp ladder of the invention (lane 3) produced enhanced resolution, in 10 bp increments, of nucleic acid size compared to other commercially available nucleic acid sizing ladders. The present ladder also produced a 100 bp band of about 2- to 3-fold higher intensity than other bands, thus providing an internal sizing reference marker in the ladder of the invention. These results indicate that the double-stranded ladder of the invention facilitates rapid analysis of the size of double-stranded nucleic acid molecules with about 10 bp resolution.

Example 3

Production and Characterization of Single-stranded Ladder

To determine the utility of the present ladder in estimating the size of single-stranded nucleic acid molecules, a single-stranded ladder was prepared as described above and end-labeled with $^{32}$P using T4 kinase. Samples of this ladder were then electrophoresed as described above.

Figure 3:
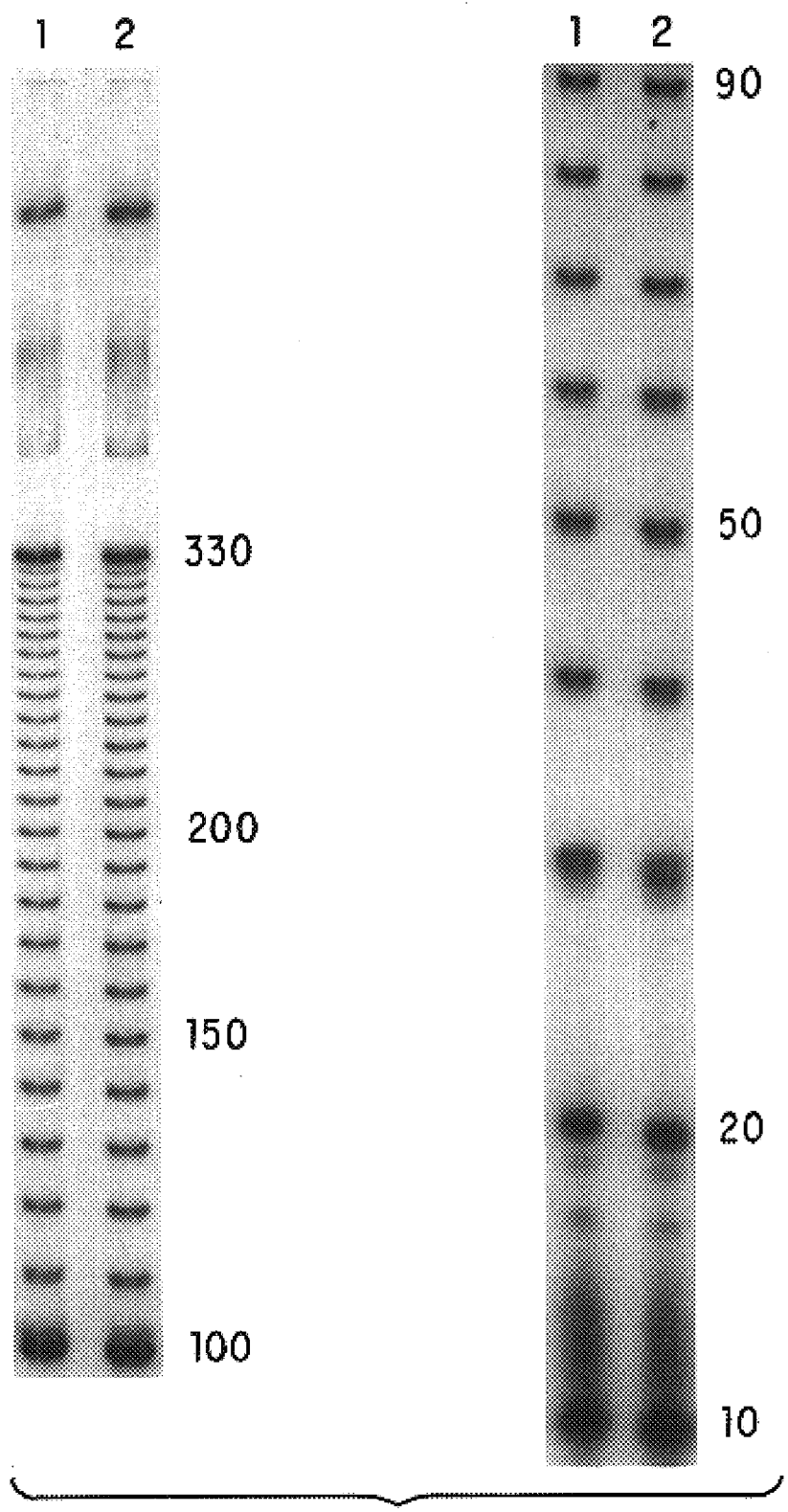
FIG. 3 depicts a $^{32}$P-labeled single-stranded 10 bp ladder of the invention (duplicate samples in lanes 1 and 2).

As shown in FIG. 3, the $^{32}$P-labeled single-stranded ladder produced clearly resolved bands in the gel in 10 nucleotide increments. The range of sizes easily resolvable with this ladder was from about 10 nucleotides to about 330 nucleotides. These results demonstrate that the single-stranded ladder of the invention facilitates rapid analysis of the size of single-stranded nucleic acid molecules with about 10 bp resolution.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A nucleic acid molecule comprising multiple copies of a repeat-containing sequence and multiple restriction enzyme cleavage sites, wherein said repeat-containing sequence is a double-stranded polynucleotide having from about 5 to about 1000 base pairs, and wherein the top strand of said repeat-containing sequence has substantially the same percentage of each respective nucleotide as in the bottom strand, and wherein said restriction sites are created by the junction of adjacent copies of said repeat-containing sequence.

2. The nucleic acid molecule of claim 1, wherein said nucleic acid molecule is a DNA molecule.

3. The nucleic acid molecule of claim 1, wherein said nucleic acid molecule is an RNA molecule.

4. The nucleic acid molecule of claim 1, wherein said nucleic acid molecule is a DNA-RNA hybrid molecule.

5. The nucleic acid molecule of claim 1, wherein said repeat-containing sequence is a double stranded polynucleotide having from about 5 to about 100 base pairs.

6. The nucleic acid molecule of claim 1, wherein said repeat-containing sequence is a double stranded polynucleotide having about 10 base pairs.

7. The nucleic acid molecule of claim 1, wherein said repeat-containing sequence comprises a palindromic nucleotide sequence.

8. The nucleic acid molecule of claim 1, wherein said repeat-containing sequence is selected from the group consisting of: ATCTCAGGAT (SEQ ID NO: 1), ATCAGTCGAT (SEQ ID NO: 2), ATCGCATGAT (SEQ ID NO: 3), ATCATGCGAT (SEQ ID NO: 4), the cormplement of SEQ ID NO:1, the complement of SEQ ID NO: 2, the complement of SEQ ID NO: 3 and the complement of SEQ ID NO: 4.

9. The nucleic acid molecule of claim 1, wherein said nucleic acid molecule comprises from about 2 to about 500 copies of said repeat-containing sequence.

10. The nucleic acid molecule of claim 1, wherein said nucleic acid molecule comprises from about 20 to about 100 copies of said repeat-containing sequence.

11. The nucleic acid molecule of claim 1, wherein said nucleic acid molecule comprises from about 200 to about 300 copies of said repeat-containing sequence.

12. The nucleic acid molecule of claim 1, wherein said restriction site is a restriction site that produces blunt-ends upon restriction digestion.

13. The nucleic acid molecule of claim 12, wherein said restriction site is selected from the group consisting of: AluI, DraI, Eco47III, EcoRV, FspI, HpaI, MscI, NruI, PvuII, RsaI, ScaI, SmaI, SspI, StuI and ThaI.

14. The nucleic acid molecule of claim 1, wherein said restriction site is a restriction site that produces sticky-ends upon restriction digestion.

15. The nucleic acid molecule of claim 14, wherein said restriction site is selected from the group consisting of: AvaI, BamHI, BanII, BglII, ClaI, EcoRI, HindIII, HpaII, KpnI, MseI, NcoI, NdeI, NotI, PstI, PvuI, SacI, SalI, XbaI and XhoI.

16. The nucleic avid molecule of claim 1, wherein said nucleic acid molecule is in circular form.

17. The nucleic acid molecule of claim 1, wherein said nucleic acid molecule is in linear form.

18. A sizing ladder comprising two or more nucleic acid fragments, wherein said sizing ladder is produced by at least partially digesting the nucleic acid molecule of claim 1 with a restriction endonuclease that cleaves at said restriction site.

19. The sizing ladder of claim 18, wherein said two or more nucleic acid fragments are of varying sizes, and wherein the size of each nucleic acid fragment is a multiple of the size of said repeat-containing sequence.

20. The sizing ladder of claim 19, wherein said sizing ladder comprises multiple nucleic acid fragments increasing in size by 10 base pair increments, the largest fragment being 330 base pairs in length.

21. The sizing ladder of claim 18, wherein said nucleic acid fragments are single stranded.

22. The sizing ladder of claim 21, wherein said nucleic acid fragments are detectably labeled.

23. The sizing ladder of claim 22, wherein said nucleic acid fragments are detectable labeled with a radiolabel, a fluorescent label or a chemiluminescent label.

24. A kit comprising one or more containers, wherein a first container contains the sizing ladder of claim 18.

25. The sizing ladder of claim 18, wherein said nucleic acid fragments are detectably labeled.

26. The sizing ladder of claim 25, wherein said nucleic acid fragments are detectably labeled with a radiolabel, a fluorescent label or a chemiluminescent label.

27. A method for detennining the size of a nucleic acid molecule, said method comprising:
   (a) separating the sizing ladder of claim 18 and said nucleic acid molecule according to size; and
   (b) determining the size of said nucleic acid molecule by comparison to said sizing ladder.

28. The method of claim 27, wherein said separating is accomplished by electrophoresis on an agarose gel.

29. The method of claim 27, wherein said separating is accomplished by electrophoresis on an a polyacrylamide gel.

30. The nucleic acid molecule of claim 1, wherein said nucleic acid molecule is a cosmid or plasmid.

31. A host cell comprising the nucleic acid molecule of claim 1.

32. A method for making a sizing ladder, said method comprising:
   (a) mixing the nucleic acid molecule of claim 1 with a restriction enzyme that cleaves at said restriction site; and
   (b) incubating said mixture under conditions favoring the cleavage of said nucleic acid molecule at said restriction site.

33. The method of claim 32, further comprising treating said mixture under conditions favoring the formation of single-stranded nucleic acid molecules.

34. The method of claim 33, wherein said conditions favoring the formation of single-stranded nucleic acid molecules are heat denaturation or chemical denaturation.

35. A kit comprising one or more containers, wherein a first container contains the nucleic acid molecule of claim 1.

36. The nucleic acid molecule of claim 1, wherein said nucleic acid molecule is linear.

37. A vector comprising a nucleic acid molecule comprising multiple copies of a repeat-containing sequence and multiple restriction enzyme cleavage sites, wherein said repeat-containing sequence is a double-stranded polynucleotide having from about 5 to about 1000 base pairs; and wherein the top strand of said repeat-containing sequence has substantially the same percentage of each respective nucleotide as in the bottom strand, and wherein said restriction sites are created by the junction of adjacent copies of said repeat-containing sequence.

38. The vector of claim 37, wherein said vector comprises one or more origins of replication or one or more selectable markers.

39. A host cell comprising the vector of claim 37.

40. A sizing ladder comprising two or more nucleic acid fragments, wherein said sizing ladder is produced by at least partially digesting the vector of claim 37 with a restriction endonuclease that cleaves at said restriction site.

41. The vector pA102.4.

42. A method for making a sizing ladder, said method comprising:

(a) mixing the vector of claim 41 with a restriction enzyme that cleaves at a restriction site of said vector; and (b) incubating said mixture under conditions favoring the cleavage of said nucleic acid molecule at said restriction site.

43. A kit comprising one or more containers, wherein a first container contains the vector of claim 41.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 10 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:1:

ATCTCAGGAT          10

(2) INFORMATION FOR SEQ ID NO:2:

(i) SEQUENCE CHARACTERISTICS:
        (A) LENGTH: 10 base pairs

```
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:2:

ATCAGTCGAT                                                                10

(2) INFORMATION FOR SEQ ID NO:3:

(i) SEQUENCE CHARACTERISTICS:
        (A) LENGTH: 10 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:3:

ATCGCATGAT                                                                10

(2) INFORMATION FOR SEQ ID NO:4:

(i) SEQUENCE CHARACTERISTICS:
        (A) LENGTH: 10 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:4:

ATCATGCGAT                                                                10

(2) INFORMATION FOR SEQ ID NO:5:

(i) SEQUENCE CHARACTERISTICS:
        (A) LENGTH: 65 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:5:

AATTCTCGGG ATATCTCAGG ATATCTCAGG ATATCTCAGG ATATCTCAGG ATATCTCGGG          60

CTGCA                                                                     65

(2) INFORMATION FOR SEQ ID NO:6:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CAACAACAAG AATTCAGGCC TAGCCAGTGC CTCGTCCATT TTT                            43

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
```

-continued

```
    (D) TOPOLOGY: linear (ii) MOLECULE TYPE: cDNA (xi) SEQUENCE DESCRIPTION: SEQ ID NO:7:

CAACAACAAA AGCTTCTTAC ATGGCCCAGG TGCAGTA                                   37
```